US00PP10536P

United States Patent [19]

Danziger

[11] Patent Number: Plant 10,536

[45] Date of Patent: Aug. 4, 1998

[54] NEW GUINEA IMPATIENS PLANT NAMED 'DANIMAZ'

[75] Inventor: Gaby Danziger, Nir Zvi, Israel

[73] Assignee: Danziger—"Dan" Flower Farm, Post Beit Dagan, Israel

[21] Appl. No.: 677,850

[22] Filed: Jul. 10, 1996

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 8,111 1/1993 Dehan ..... Plt./87.6

P.P. 10,110 11/1997 Trees ..... Plt./87.6

*Primary Examiner*—Howard J. Locker

*Assistant Examiner*—Kent L. Bell

*Attorney, Agent, or Firm*—Foley & Lardner

[57] ABSTRACT

A new and distinct cultivar of Impatiens plant named 'Danimaz', characterized by the combined features of bright red flower color, relatively large flowers, solid dark green leaves, and by its round, compact growth habit but relatively large plant diameter, with the flowers developing slightly above the foliage.

1 Drawing Sheet

1

The present invention relates to a new and distinctive cultivar of Impatiens plant, botanically known as Impatiens, commercially known as New Guinea Impatiens, and known by the cultivar name 'Danimaz'.

Danimaz was developed by the inventor Gaby Danziger in a controlled breeding program in Mishmar Hashiva, Israel by crossing the cultivar identified as '2-95', (seed parent), with the cultivar identified as '6-83' (pollen parent). Both cultivars are proprietary.

Asexual reproduction of the new cultivar by leaf cuttings taken by the inventor at Mishmar Hashiva, Israel has shown that the unique features of this new Impatiens plant are stabilized and are reproduced true to type in successive propagations.

The following characteristics in combination distinguish the new Impatiens plant from both its parent varieties and other cultivated impatiens of this type known and used in the floriculture industry:

1. Deep red flower color, and relatively large individual flowers.
2. Solid dark green leaves of medium size.
3. Compact growth habit.
4. Relatively large plant diameter and round shape.

In the accompanying colored photographic drawing, the photograph comprises a top view showing the overall appearance of the new cultivar.

In the photograph, color is as true as it is reasonably possible to obtain in a colored reproduction of this type. It is anticipated that this plant will be marketed under the trademark "Mazurka".

When compared to the cultivar Rondo, disclosed in United States Plant Pat. No. 8,111, Danimaz has a lighter bright red flower color, a more compact growth habit, longer and narrower leaves, and earlier flowering.

The following is a detailed description of my new Impatiens cultivar based on plants produced under commercial practice in Mishmar Hashiva, Israel. The plants were grown in a net-covered greenhouse during spring time, with a maximum temperature of 30° C and a minimum temperature of 18° C.

2

Color references are made to The Royal Horticultural Society Colour Chart except where general terms of ordinary dictionary significance are used.

Parentage: Seedling from '2-'95×'6-83'.

Propagation:

*Type cutting.*—Leaf cuttings.

*Time to initiate roots.*—7–8 days at 25° C in summer and 8–9 days at 20° C in winter.

*Rooting habit.*—Roots well, about 20–25 roots per plant, each approximately 2–3 cm in length and 0.5–1.0 mm thick.

Plant description:

*Form.*—Plant is relatively large in diameter and round, with good self branching. As measured 4 months after planting a single young plant in a 16 cm pot, the plant was approximately 16–25 cm in height and 21–60 cm in width.

*Habit.*—Compact.

*Foliage (mature).*—Size: Approximately 90 mm long and 35 mm wide, leaf apex is acuminate and base is acuminate; texture is typical for the species. Shape: Oblong. Margin: Serrated. Color: Young foliage, top side 137A, under side 137C; mature foliage, top side 139A, under side 139C. Venation: Pinnate; in the top side of leaf the main vein is red, becoming green; veins emanating from main vein are very thin, green and feathered; on bottom side of leaf, main vein is red.

Flowering description:

*Flowering habits.*—Flowers develop only slightly above the foliage, and cover the entire plant.

*Natural flowering season.*—Flowering is year around in temperatures between 5° C and 25° C; not tolerant to frost.

*Flower buds.*—There are 3–6 buds on each of 8–12 leaf axils, with each bud before opening being oval shape and 1.5 cm in length along its major axis. Buds are carried on green pedicels 35 mm in length, with red spurs (RHS 46A). Spur is half-rounded in shape and 3.0–3.5 cm in length.

*Flower borne.*—The flowers are carried on stems that terminate slightly above the foliage. Flowering commences 51 days after planting under normal growing conditions.

*Quantity of flowers.*—Medium. At the time of maximum flowering, the numbers of flowers per plant is 25–70.

*Petals.*—Shape: Typical, two heart-shaped pairs of petals, with each petal being approximately 2.3–2.7 cm in width and 2.0–2.2 cm in length, the remaining petal is relatively larger at 3.5 cm in width and 2.0 cm in length. Color: Top side when opening 45A, with no fading; under side slightly lighter. Number of petals: 5. Size of flowers: Large, approximately 5.5 cm in diameter.

*Reproductive organs.*—Stamens: One (1) in number. Another shape: Round, color red. Pollen color: White. Pistils: Stigma shape: Round, color nearly white. Style color: Green. Ovaries: Four, 1 mm in size, green in color.

*Disease resistance.*—No abnormal disease problems have been noted to date.

I claim:

1. A new and distinct cultivar of Impatiens plant named 'Danimaz', as illustrated and described.

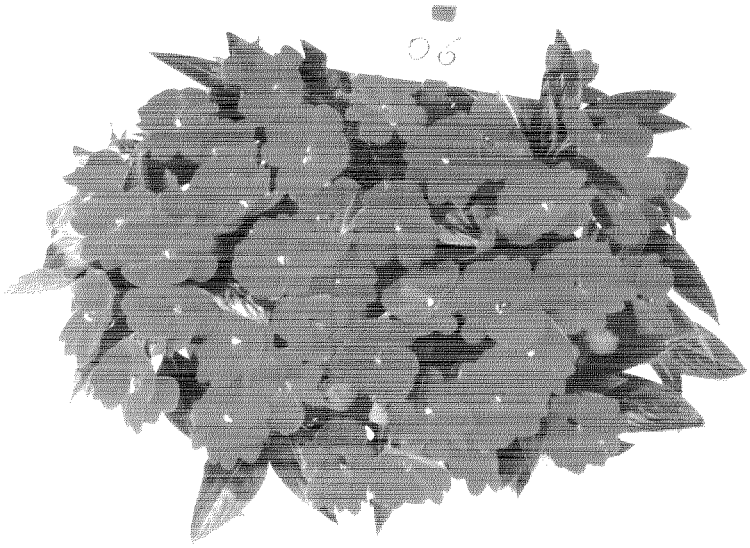

* * * * *